US007767390B2

(12) United States Patent
Kopreski

(10) Patent No.: US 7,767,390 B2
(45) Date of Patent: *Aug. 3, 2010

(54) METHODS FOR EVALUATING DRUG-RESISTANCE GENE EXPRESSION IN THE CANCER PATIENT

(75) Inventor: Michael S. Kopreski, Long Valley, NJ (US)

(73) Assignee: OncoMEDx, Inc., Long Valley, NJ (US)

( * ) Notice: Subject to any disclaimer, the term of this patent is extended or adjusted under 35 U.S.C. 154(b) by 616 days.

This patent is subject to a terminal disclaimer.

(21) Appl. No.: 10/299,559

(22) Filed: Nov. 19, 2002

(65) Prior Publication Data

US 2003/0148345 A1 Aug. 7, 2003

Related U.S. Application Data

(60) Provisional application No. 60/331,862, filed on Nov. 20, 2001.

(51) Int. Cl.
*C12Q 1/68* (2006.01)
*C12P 19/34* (2006.01)

(52) U.S. Cl. .......................................... 435/6; 435/91.2
(58) Field of Classification Search ........................ None
See application file for complete search history.

(56) References Cited

U.S. PATENT DOCUMENTS

| 5,665,549 | A | 9/1997 | Pinkel |
| 6,159,685 | A | 12/2000 | Pinkel |
| 6,329,179 | B1 | 12/2001 | Kopreski |
| 6,335,167 | B1 | 1/2002 | Pinkel |

FOREIGN PATENT DOCUMENTS

| DE | 3717212 A1 | 12/1988 |
| WO | WO 90/09456 A1 | 8/1990 |
| WO | 97/35589 A | 10/1997 |
| WO | 98/14617 A | 4/1998 |

OTHER PUBLICATIONS

Theodor et al., Detection of pancreatic carcinoma: Diagnostic value of K-ras mutations in circulating DNA from serum. Diges. Dis. Sci. (1999) 44: 2014-2019.*
Kobayashi et al., Competitive reverse transcription-polymerase chain reaction assay for quantification of human multidrug resistance 1 (MDR1) gene expression in fresh leukemic cells. J. Lab. Clin. Med. (2000) 135: 199-209.*
Kubo et al., Point mutations of the topoisomerase II alpha gene in patients with small cell lung cancer treated with etoposide. Cancer Res. (1996) 56: 1232-1236.*
Zhou et al. Circulating RNA as a novel tumor marker: An in vitro study of the origins and characteristics of extracellular RNA. Cancer Letters (2008) 259:50-60.*
Komeda et al., "Sensitive Detection of Circulating Hepatocellular Carcinoma Cells in Peripheral Venous Blood," *Blood* 2214-19.
Hasselmann et al., "Detection of tumor-associated circulating mRNA in serum, plasma and blood cells from patients with disseminated malignant melanoma," *Oncology Reports* 8:115-18 (2001).
Kopreski et al., "Detection of Tumor Messenger RNA in the Serum of Patients with Malignant Melanoma," *Clinical Cancer Research* 5:1961-65 (Aug. 1991).
Chen et al., "Telomerase RNA as a Detection Marker in the Serum of Breast Cancer Patients," *Clinical Cancer Research* 6:3823-26 (Oct. 2000).
Kamm et al. "Nucleic Acid Concentrations in Normal Human Plasma," *Clinical Chemistry* 18(6) 519-522 91972).
Kopreski et al., "Detection of tumor messenger RNA in the serum of patients with malignant melanoma." Clinical Cancer Research 5:1961-65 (Aug. 1999) 5:1961-65.
Leitzel et a., "Detection of cancer cells in peripheral blood of breast cancer patients using reverse transcription-polymerase chain reaction for epidermal growth factor receptor." Clinical Cancer Research 4:3037-43 (Dec. 1998).
Tamamiyagi et al., "Quantitative analysis of ferrochelatase mRNA in blood cells of erythropoietic protoprophyria patients." Journal of Dermatological Science 11(2)154-60 (Feb. 1996).
Garbarz et al.,"Spectrin Beta-Tandil A Novel Shortened Beta-Chain Variant Associated with Hereditary Elliptocytosis is due to a Deletional Frameshift Mutation in the Beta Spectrin Gene," Blood 80(4)1066-73 (1992).
Monteyne et al., "Expression of costimulatory molecules and cytokines in CSF and peripheral blood mononuclear cells from multiple sclerosis patients" Acta Neurological Belgica 1(99):11-20 (Mar. 1999).

(Continued)

*Primary Examiner*—Kenneth R. Horlick
*Assistant Examiner*—David C Thomas
(74) *Attorney, Agent, or Firm*—McDonnell Boehnen Hulbert & Berghoff

(57) ABSTRACT

The methods of the invention detect in a qualitative or quantitative fashion drug-resistance RNA and DNA in blood plasma, serum, and other bodily fluids. The methods of the invention thereby enable the assessment of drug resistance in a neoplasm without the requirement of a tissue biopsy. The inventive methods are useful for the evaluation, monitoring, and selecting of drug treatment regimens, and for determining a predisposition for or prognosis of chemoresistant neoplastic disease.

38 Claims, No Drawings

OTHER PUBLICATIONS

Serra et al., "Multiple sclerosis and multiple sclerosis-associated retrovirus in Sardinia" Neurological Sciences 22(2) 171-73 (Apr. 2001).

Kopreski et al., "Cellular-versus extracellular-based assays. Comparing utility in DNA and RNA molecular marker assessment" Annals of New York Academy of Sciences 906:124-8 (Apr. 2000).

Messner et al., "Expression of messenger RNA of the cardiac isoforms of troponin T and I in myopathic skeletal muscle" American Journal of Clinical Pathology 114(4)544-49(Oct. 2000).

Kamm et al., "Nucleic-Acid Concentrations in Normal Human Plasma" Clinical Chemistry 18(6)519-22 (1972).

Shutack et al., "A Study of the RNA levels of normal blood serum" The Journal of the American Osteopathic Association 67(9)1051-53 (May 1968).

Guin et al., "Electrophoretic Characterization of Plasma RNA" Biochemical Medicine 13(3)224-30 (1975).

Stroun et al., "Presence of RNA in the nucleoprotein complex spontaneously released by human lymphocytes and frog auricles in culture" Cancer Research 38(10)3546-3554 (Oct. 1978).

Allouche et al., "Expression of basic fibroblast growth factor (bFGF) and FGF-receptors in human leukemic cells" Leukemia:Official Journal of the Leukemia Society of America, Leukemia Reserach Fund 9(1)77-86 (Jan. 1995).

Ricchiuti et al., "Expression of cardiac troponin T mRNA in skeletal muscle from patients with end stage renal disease and muscular dystrophy" Clinical Chemistry 45(6)A144-A145 (Jun. 1999).

Ricchiuti et al., "RNA expression of cardiac troponin T isoforms in diseased human skeletal muscle" Clinical Chemistry 45(12)2129-35 (Dec. 1999).

Ricchiuti et al., "Cardiac troponin I and T alterations in hearts with severe left ventricular remodeling" Clinical Chemistry 43(6)990-95 (1997).

Rosenzweig et al., "Preclinical Diagnosis of Familial Hypertrophic Cardiomyopathy by Genetic Analysis of Blood Lymphocytes" New England Journ of Med 325(25)1753-60 (Nov. 19, 1981).

Spiegelman et al., "The Development and Use of and Extracellular RNA Replicating System" The Harvey Lectures No. 64 pp. 1-67 (1969).

Komeda et al., "Sensitive Detection of Circulating Hepatocellular Carcinoma Cells in Peripheral Venous Blood," *Blood* 2214-19, (1995).

Hasselmann et al., "Detection of tumor-associated circulating mRNA in serum, plasma and blood cells from patients with disseminated malignant melanoma," *Oncology Reports* 8:115-18 (2001).

Kopreski et al., "Detection of Tumor Messenger RNA in the Serum of Patients with Malignant Melanoma," *Clinical Cancer Research* 5:1961-65 (Aug. 1991).

Chen et al., "Telomerase RNA as a Detection Marker in the Serum of Breast Cancer Patients," *Clinical Cancer Research* 6:3823-26 (Oct. 2000).

Kamm et al. "Nucleic Acid Concentrations in Normal Human Plasma," *Clinical Chemistry* 18(6) 519-522 91972), (1972).

Pfleiderer et al., "Detection of Tumour Cells in Peripheral Blood and Bone Marrow from Ewing Tumour Patients by RT-PCR," *Int. J. Cancer* 64:135-139 (1995).

Hla et al., "Human cyclooxygenase-2 cDNA," *Proc. Natl. Acad. Sci.* 89:7384-88 (Aug. 1992).

Subbarayan et al., "Differential Expression of Cyclooxygenase-2 and Its Regulation by Tumor Necrosis Factor-$\alpha$ in Normal and Malignant Prostate Cells," *Cancer Research* 61:2720-26 (Mar. 15, 2001).

Yoshimura et al., "Expression of Cyclooxygenase-2 in Prostrate Carcinoma," *American Cancer*, 589-96 (2000).

Agoff et al., "The Role of Cyclooxygenase 2 in Ulcerative Colitis-Associated Neoplasia," *American Journal of Pathology* 157(3) 737-745 (Sep. 2000).

Lim et al., "Nuclear Fator-KB Regulates Cyclooxygenase-2 Expression and Cell Proliferation in Human Gastric Cancer Cells," *Laboratory Investigation* 81(3) 349-360 (2001).

Sales et al., "Cyclooxygenase-2 Expression and Prostaglandin E2 Synthesis Are Up-Regulated in Carcinomas of the Cervix: A Possible Autocrine/Paracrine Regulation of Neoplastic Cell Function via EP2/EP4 Receptors," *The Journal of Clinical Endocrinology & Metabolism* 86(5) 2243-49 (2001).

Souza et al., "Selective Inhibition of Cyclooxygenase-2 Suppresses Growth and Induces Apoptosis in Human Esophageal Adenocarcinoma Cells," *Cancer Research* 60:5767-72 (Oct. 15, 2000).

* cited by examiner

SEQUENCE LISTING

<160> NUMBER OF SEQ ID NOS: 2

<210> SEQ ID NO 1
<211> LENGTH: 25
<212> TYPE: DNA
<213> ORGANISM: Homo sapiens

<400> SEQUENCE: 1
cggaaaccat ccacgaccct aatcc                                         25

<210> SEQ ID NO 2
<211> LENGTH: 25
<212> TYPE: DNA
<213> ORGANISM: Homo sapiens

<400> SEQUENCE: 2
acctcctcat tcgcatccac cttgg                                         25

METHODS FOR EVALUATING DRUG-RESISTANCE GENE EXPRESSION IN THE CANCER PATIENT

This application claims priority to U.S. Provisional Application. Ser. No. 60/331,862, filed Nov. 20, 2001.

BACKGROUND OF THE INVENTION

Cancer is a leading cause of death in the world. Despite the development of newer chemotherapeutic agents and combination chemotherapy regimens, metastatic neoplastic diseases are often resistant to therapy. The reasons for this drug-resistance are two-fold. First, specific genes may be expressed that impart drug-resistant characteristics to the neoplastic tissue. Second, tumors are often heterogeneous tissues in their sensitivity to specific chemotherapeutic agents. Treatment over time thus selects out the resistant tissue. An understanding of drug-resistance gene expression within a tumor over time thus is of importance in developing appropriate treatment regimens for the patient. Current methods for evaluating the drug-resistance phenotype of a patient's tumor require the analysis of a tissue specimen obtained by an invasive biopsy of the tumor. The invasive nature of these biopsies often precludes the serial longitudinal monitoring of drug-resistance in a given patient, and further, is prone to sampling error.

This invention relates to methods for evaluating the expression of drug-resistance genes (drug-resistance-associated genes) in neoplastic tissue without the requirement of tissue biopsy. Specifically, the invention provides for the detection and monitoring of drug-resistance gene nucleic acid, particularly ribonucleic acid (RNA) or deoxyribonucleic acid (DNA), in a bodily fluid from an animal or human. Since bodily fluids such as blood, plasma, serum, urine, saliva, cerebrospinal fluid, and effusions are more easily and readily obtainable than most tissue specimens, the invention provides a convenient method of evaluating a tumor's drug-resistance, and thereby of selecting, monitoring, or altering drug therapies such as chemotherapy. Furthermore, the invention provides a method to evaluate drug-resistance expression of the entire tumor-burden of an animal, preferably a human, thereby reducing sampling bias induced by tumor heterogeneity, as may occur during analysis of localized tumor biopsies. The invention therefore provides methods for evaluating the presence of RNA and mutated or altered or polymorphic DNA associated with drug-resistance genes in bodily fluid, particularly blood, plasma, serum, and other bodily fluid, wherein said genes include but are not limited to the multidrug resistance 1 gene (MDR-1), said gene encoding the 170 kD transport protein P-glycoprotein (Pgp), the multidrug resistance-associated protein gene (MRP) encoding a 190 kD adenosine triphosphate binding transport protein with homology to MDR-1, and further associated genes encoding the multidrug resistance proteins MRP1, MRP2, MRP3, and MRP5, the topoisomerase I gene, the topoisomerase II alpha and beta genes, genes associated with glutathione metabolism (GSH genes) including the glutathione S-transferase genes, the thymidylate synthase gene (TS), the thymidine phosphorylase gene (TP), and the dihydropyrimidine dehydrogenase gene (DPD), said gene RNAs being characterized as tumor-associated RNA or DNA herein. Co-owned and co-pending U.S. patent application Ser. No. 09/155,152, incorporated herein by reference in its entirety, detects tumor-associated RNA in bodily fluids such as blood plasma and serum, wherein said RNA detection is used for detecting, monitoring, or evaluating cancer or premalignant conditions.

In the present invention, methods for detecting extracellular nucleic acids are utilized in a novel manner to determine drug-resistance gene expression in a patient. Furthermore, a novel method is described herein that enables evaluation of drug-resistance gene expression in a tumor without the need of directly obtaining tumor tissue.

There is a newly-appreciated need in the art to identify drug-resistance propensity in an animal, most preferably a human, in a safe and convenient manner by detecting in a qualitative or quantitative fashion drug-resistance gene RNA and DNA such as MDR-1 RNA, MRP RNA, associated MRP1 RNA, MRP2 RNA, MRP3 RNA, MRP5 RNA, GSH transferase RNA, TS RNA, TP RNA, DPD RNA, mutated topoisomerase I RNA or DNA, mutated topoisomerase II alpha and beta RNA and DNA, and other mutated or altered DNA in bodily fluids such as whole blood or blood plasma or serum, including DNA polymorphisms including but not limited to MDR-1 polymorphisms, GSH-associated gene polymorphisms including GSH-S transferase polymorphisms, TS polymorphisms, and MDR-1 polymorphisms. Further, there is a need in the art to evaluate the predisposition in an animal, most preferably a human, to respond favorably or unfavorably to a particular chemotherapy regimen by detecting drug-resistance gene RNA or mutated or altered or polymorphic DNA in bodily fluids such as blood plasma or serum, thereby enabling particular treatment regimens to chosen.

SUMMARY OF THE INVENTION

The present invention describes a method of evaluating an animal, most preferably a human, for drug-resistance gene expression by detecting nucleic acids (mRNA and mutated, altered, or polymorphic DNA) of genes associated with drug-resistance in bodily fluids, preferably blood and most preferably blood plasma and serum as well as in other bodily fluids, preferably urine, effusions, ascites, saliva, cerebrospinal fluid, cervical, vaginal, and endometrial secretions, gastrointestinal secretions, breast secretions, and bronchial secretions. The invention thereby provides a method for detecting, evaluating, or monitoring drug-resistance gene expression in a tumor without the requirement that tumor tissue be first directly obtained. Specific drug-resistance associated nucleic acids are recognized to include MDR-1 RNA, MRP RNA, associated MRP1 RNA, MRP2 RNA, MRP3 RNA and MRP5 RNA, GSH RNA including GSH S-transferase RNA, TS RNA, TP RNA, DPD RNA, mutated topoisomerase I RNA and DNA, mutated topoisomerase II alpha and beta RNA and DNA, MDR-1 polymorphisms, TS polymorphisms, and GSH S-transferase polymorphisms.

The invention provides the method of amplifying and detecting extracellular drug-resistance gene RNA and DNA, wherein said RNA include but are not limited to MDR-1 RNA, MRP RNA, associated MRP1 RNA, MRP2 RNA, MRP3 RNA, MRP5 RNA, GSH RNA, TP RNA, DPD RNA TS RNA, and topoisomerase I and II RNA, and said DNA is a mutated, altered, or polymorphic DNA including but not limited to mutated topoisomerase I DNA, mutated topoisomerase II alpha DNA, MDR-1 polymorphisms, TS polymorphisms, and GSH S-transferase polymorphisms. In a preferred embodiment, the present invention provides a method for detecting drug-resistance gene RNA and mutated, altered, or polymorphic DNA in blood or a blood fraction, including plasma and serum, or in other bodily fluids, the method comprising the steps of extracting RNA and DNA from blood, plasma, serum, or other bodily fluid, in vitro amplifying in a qualitative or quantitative fashion one or more drug resistance gene mRNA or their cDNA or mutated drug resistance gene DNA, and detecting the amplified product of the drug-resistance gene mRNA or its cDNA, or the drug resistance gene DNA. Said amplification methods may further include the qualitative or quantitative comparison to a reference RNA or DNA species normally present in the plasma, serum, or bodily fluid of individuals with or without cancer.

In a first aspect of this embodiment, the present invention provides methods for detecting drug-resistance gene RNA in blood or blood fractions, including plasma and serum, in a human or animal. Said methods are useful for detecting, monitoring, or evaluating drug-resistance in various proliferative disorders, particularly stages of neoplastic disease, including premalignancy, early cancer, non-invasive cancer, carcinoma in-situ, invasive cancer and advanced cancer. In this aspect, the method comprises the steps of extracting RNA from blood or blood plasma or serum, in vitro amplifying or signal amplifying drug-resistance gene RNA comprising the extracted RNA either qualitatively or quantitatively wherein drug-resistance gene RNA includes but is not limited to MDR-1 RNA, MRP RNA, associated MRP1 RNA, MRP2 RNA, MRP3 RNA, MRP5 RNA, GSH RNA, TP RNA, DPD RNA, TS RNA, and topoisomerase I and II RNA, and detecting the amplified product of drug-resistance gene RNA or its cDNA.

The invention in a second aspect provides a method for detecting drug-resistance gene RNA in any bodily fluid. Preferably, said bodily fluid is whole blood, blood plasma, serum, urine, effusions, ascitic fluid, saliva, cerebrospinal fluid, cervical secretions, vaginal secretions, endometrial secretions, gastrointestinal secretions, bronchial secretions including sputum, or secretions or washings from the breast from a human or animal. In this aspect, the method comprises the steps of extracting RNA from the bodily fluid, in vitro amplifying or signal amplifying drug-resistance gene RNA comprising a fraction of the extracted RNA, or preferably the corresponding cDNA into which the RNA is converted, in a qualitative or quantitative fashion, and detecting the amplified product of drug-resistance gene RNA or cDNA, wherein drug-resistance gene RNA includes but is not limited to MDR-1 RNA, MRP RNA, associated MRP1 RNA, MRP2 RNA, MRP3 RNA, MRP5 RNA, GSH RNA, TP RNA, DPD RNA, TS RNA, and topoisomerase I and II RNA. In these embodiments, the inventive methods are particularly advantageous for detecting, monitoring, or evaluating drug-resistance in various proliferative disorders, particularly stages of neoplastic disease, including premalignancy, early cancer, non-invasive cancer, carcinoma-in-situ, invasive cancer and advanced cancer, without the requirement of a tissue specimen.

In a third aspect of this embodiment, the present invention provides methods for detecting mutated, altered, or polymorphic drug-resistance gene DNA in blood or blood fractions, including plasma and serum, in a human or animal. Said methods are useful for detecting, monitoring, or evaluating drug-resistance in various proliferative disorders, particularly stages of neoplastic disease, including premalignancy, early cancer, non-invasive cancer, carcinoma in-situ, invasive cancer, and advanced cancer. In this aspect, the method comprises the steps of extracting DNA from blood or blood plasma or serum, in vitro amplifying or signal amplifying mutated, altered, or polymorphic drug-resistance gene DNA comprising the extracted DNA either qualitatively or quantitatively wherein mutated, altered, or polymorphic drug-resistance gene DNA includes but is not limited to mutated topoisomerase I gene DNA, mutated topoisomerase II gene DNA,. MDR-1 polymorphic DNA, GSH polymorphic DNA such as GSH S-transferase polymorphisms, and TS polymorphic DNA, and detecting the amplified product of the drug-resistance gene DNA.

The invention in a fourth aspect provides a method for detecting mutated, altered, or polymorphic drug-resistance gene DNA in any bodily fluid. Preferably, said bodily fluid is whole blood, blood plasma, urine, effusions, ascitic fluid, saliva, cerebrospinal fluid, cervical secretions, vaginal secretions, endometrial secretions, gastrointestinal secretions, bronchial secretions including sputum, or secretions or washings from the breast from a human or animal. In this aspect, the method comprises the steps of extracting DNA from the bodily fluid, in vitro amplifying or signal amplifying mutated, altered, or polymorphic drug-resistance gene DNA comprising a fraction of the extracted DNA in a qualitative or quantitative fashion, and detecting the amplified product of the mutated, altered, or polymorphic drug-resistance gene DNA. In these embodiments, the inventive methods are particularly advantageous for detecting, monitoring, or evaluating drug-resistance in various proliferative disorders, particularly stages of neoplastic disease, including premalignancy, early cancer, non-invasive cancer, carcinoma-in-situ, invasive cancer, and advanced cancer, without the requirement of a tissue specimen.

The method of the invention is additionally useful for identification of drug-resistance gene RNA-expressing tissue or mutated, altered, or polymorphic drug-resistance gene DNA-expressing tissue in an animal, most preferably a human, in a manner that avoids sampling errors associated with tissue biopsy, wherein detection of drug-resistance gene RNA or DNA in a bodily fluid from said animal thereby identifies drug-resistance gene RNA-expressing tissue or drug-resistance gene DNA-expressing tissue in said animal.

The invention provides primers and probes useful in the efficient amplification of extracellular MDR-1, MRP or MRP1, MRP2, MRP3, MRP5, TP, TS, DPD, GSH, and/or topoisomerase I and II mRNA or cDNA, from bodily fluid, most preferably blood plasma or serum.

The invention further provides a diagnostic kit for detecting drug-resistance gene nucleic acid in bodily fluid, preferably blood plasma or serum, wherein the kit comprises primers, probes or both primers and probes for amplifying and detecting extracellular drug-resistance gene RNA or cDNA derived therefrom, or mutated, altered, or polymorphic gene DNA, and/or reagents for extracting said nucleic acids from the bodily fluid. In a first aspect of this embodiment, the drug-resistance gene is one selected from the drug-resistance genes MDR-1, MRP, those encoding the multidrug resistance proteins MRP1, MRP2, MRP3, MRP5, glutathione S-transferase, the TP-encoding gene, the TS-encoding gene, the DPD-encoding gene, the topoisomerase I gene, the topoisomerase I gene, and the topoisomerase II alpha or beta gene.

In preferred embodiments of the inventive methods, drug-resistance gene nucleic acid is extracted from whole blood, blood plasma or serum, or other bodily fluids using an extraction method such as but not limited to gelatin extraction method; silica, glass bead, or diatom extraction method; guanidinium thiocyanate acid-phenol based extraction methods; guanidinium thiocyanate acid based extraction methods; methods using centrifugation through cesium chloride or similar gradients; phenol-chloroform based extraction methods; or other commercially available RNA or DNA extraction methods. Extraction may further be performed using probes that specifically hybridize to a drug-resistance gene nucleic acid.

In preferred embodiments of the inventive methods, drug-resistance gene RNA or cDNA derived therefrom or mutated, altered, or polymorphic drug-resistance gene DNA is amplified or signal amplified using an amplification method such as polymerase chain reaction (PCR); reverse transcriptase polymerase chain reaction (RT-PCR); ligase chain reaction; signal amplification such as DNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; cleavase-based technology, or any combination or variation thereof.

In preferred embodiments of the inventive methods, detecting an amplification product of drug-resistance gene RNA or cDNA or mutated, altered, or polymorphic DNA is accomplished using a detection method such as gel electrophoresis; capillary electrophoresis; conventional enzyme-linked immunosorbent assay (ELISA) or modifications thereof, such as amplification using biotinylated or otherwise modified primers; nucleic acid hybridization using specific, detectably-labeled probes, such as fluorescent-, radioisotope-, or chromogenically-labeled probe; Northern blot analysis; Southern blot analysis; electrochemiluminescence; reverse dot blot detection; and high-performance liquid chromatography.

In particularly preferred embodiments of the inventive methods, drug-resistance gene RNA is converted to cDNA using reverse transcriptase following extraction of RNA from a bodily fluid and prior to amplification.

The methods of the invention are advantageously used as a predictive indicator for determining a risk for an animal, most preferably a human, for having a proliferative, premalignant, neoplastic or malignant disease comprising or characterized by the presence of drug-resistant cells. The methods of the invention are particularly useful for predicting the response or sensitivity of a malignant disease to particular chemotherapeutic agents. The methods of the invention are thereby useful for providing a prognosis of a disease, particularly cancer. The methods of the invention are further particularly useful for monitoring the sensitivity or response of a malignant or premalignant disease to a treatment regimen, and for indicating when a treatment regimen should be altered. Most preferably, the malignant or premalignant diseases, conditions or disorders advantageously evaluated or monitored using the methods of the invention are breast, prostate, ovarian, lung, cervical, colorectal, gastric, hepatocellular, pancreatic, bladder, endometrial, kidney, skin, and esophageal cancers, and premalignancies and carcinoma in-situ such as prostatic intraepithelial neoplasia (PIN), cervical dysplasia, cervical intraepithelial neoplasia (CIN), bronchial dysplasia, atypical hyperplasia of the breast, ductal carcinoma in-situ, colorectal adenoma, atypical endometrial hyperplasia, and Barrett's esophagus.

In certain preferred embodiments of the methods of the invention, drug-resistance gene RNA or cDNA derived therefrom, including but not limited to MDR-1 RNA, MRP RNA, associated MRP1 RNA, MRP2 RNA, MRP3 RNA, MRP5 RNA, GSH RNA, TP RNA, DPD RNA, TS RNA, and topoisomerase I and II RNA, is amplified in a quantitative manner, thereby enabling the quantitative comparison of the drug-resistance gene RNA present in a bodily fluid such as blood plasma or serum from an animal, most preferably a human. In these embodiments, the amount of the particular extracellular drug-resistance gene RNA detected in an individual is compared with a range of amounts of extracellular drug-resistance gene RNA detected in said bodily fluid in populations of animals known to have a premalignant, neoplastic, or malignant disease, most preferably a chemotherapy-sensitive or a chemotherapy-resistant neoplastic or malignant disease. Additionally, the amount of extracellular drug-resistance gene RNA detected in an individual is compared with a range of amounts of extracellular drug-resistance gene RNA detected in said bodily fluid in populations of animals known to be free from a chemotherapy-resistant premalignant, neoplastic, or malignant disease. In particularly preferred aspects of this embodiment, comparison of drug-resistance gene RNA is further made to a reference RNA extracted, amplified, and detected from said bodily fluid, wherein said reference RNA is not a drug-resistance gene RNA, but preferably is an RNA normally present in the bodily fluid of healthy individuals. In another aspect, said reference RNA is not a drug-resistance gene RNA, but is an RNA present in the bodily fluid of individuals with chemotherapy-sensitive cancer.

The methods of the invention provide ways to identify individuals having a drug-resistant malignancy, thereby permitting rational, informed treatment options to be used for making therapeutic decisions. In one aspect, the invention predicts drug-resistance for specific therapeutic agents or agent classes, wherein these agents or agent classes include but are not limited to anthracyclines and anthracenediones including doxorubicin, daunorubicin, epirubicin, and mitoxantrone; antimicrotubule agents including vinca alkaloids such as vincristine and vinblastine, taxanes including paclitaxel and docetaxel; estramustine; platinum analogues such as cisplatin and carboplatin; topoisomerase II inhibitors such as VP-16 and VM-26; 5-fluoropyrimidines such as 5-fluorouracil; antifolates including methotrexate; cytidine analogues; purine antimetabolites; alkylating agents including cyclophosphamide, chlorambucil, melphalan, BCNU, ifosfamide and other nitrogen mustards, busulfan, nitrosoureas; procarbazine and dacarbazine; bleomycin; dactinomycin; and camptothecins such as irinotecan and topotecan.

Another advantageous use for the methods of the invention is to provide a marker for predicting or assessing the adequacy of anticancer therapy, particularly therapies employing chemotherapeutic agents, administered preventively, curatively, or palliatively, or for determining whether additional or more advanced therapy is required. The invention therefore provides methods for developing a prognosis and plans of treatment in such patients.

The methods of the invention also allows identification or analysis of drug-resistance gene RNA, or mutated, altered, or polymorphic drug-resistance gene DNA, either qualitatively or quantitatively, in the blood or other bodily fluid of an individual, most preferably a human who has completed therapy, as an early indicator of relapsed cancer, impending cancer relapse, or treatment failure.

Specific preferred embodiments of the present invention will become evident from the following more detailed description of certain preferred embodiments and the claims.

DETAILED DESCRIPTION OF THE INVENTION

The invention provides methods for detecting drug-resistance gene RNA, including but not limited to MDR-1 RNA, MRP RNA or MRP1 encoding gene RNA, MRP2 encoding gene RNA, MRP3 encoding gene RNA, MRP5 encoding gene RNA, glutathione S-transferase RNA, TP RNA, DPD RNA, TS RNA, and topoisomerase I and II RNA, and mutated, altered, or polymorphic drug-resistance gene DNA, including but not limited to topoisomerase I DNA, topoisomerase II alpha and beta DNA, MDR-1 polymorphisms, TS polymorphisms, and GSH S-transferase polymorphisms, in bodily fluids of an animal, most preferably a human, thereby enabling the evaluation or monitoring of drug resistance in neoplastic tissue without the requirement of a tissue biopsy.

In preferred embodiments of the methods of the invention, extracellular RNA containing drug-resistance gene RNA, or extracellular DNA containing mutated, altered, or polymorphic drug-resistance gene DNA, is extracted from a bodily fluid. This extracted RNA or DNA is then amplified or signal amplified, either after conversion into cDNA or directly, using in vitro amplification methods or signal amplification methods in either a qualitative or quantitative manner using primers or probes specific for the drug-resistance gene RNA or cDNA or mutated, altered, or polymorphic DNA of interest. The amplified product or signal is then detected in either a qualitative or quantitative manner.

In the practice of the methods of the invention, drug-resistance gene RNA or DNA may be extracted from any bodily fluid, including but not limited to whole blood, plasma, serum, urine, effusions, ascitic fluid, saliva, cerebrospinal fluid, cervical secretions, vaginal secretions, endometrial secretions, gastrointestinal secretions, bronchial secretions including sputum, breast fluid, or secretions or washings or lavages, using, for example, extraction methods described in co-owned and co-pending U.S. patent application Ser. No. 09/155,152, the entire disclosure of which is hereby been incorporated by reference. Said RNA or DNA may further be extracted from either the cellular or the extracellular fraction of the bodily fluid. In a preferred embodiment, the bodily fluid is either blood plasma or serum. It is preferred, but not required, that blood be processed soon after drawing, and preferably within three hours, as to minimize any nucleic acid degradation in the sample. In a preferred embodiment, blood is first collected by venipuncture and kept on ice until use. Preferably, within 30 minutes to one hour of drawing the blood, serum is separated by centrifugation, for example at 1100×g for 10 minutes at 4° C. When using plasma, the blood is not permitted to coagulate prior to separation of the cellular and acellular components. Serum or plasma can be frozen, for example in 1-2 ml aliquots, most preferably at −70° C. after separation from the cellular portion of blood until further assayed. When using frozen blood plasma or serum, the frozen serum or plasma is rapidly thawed, for example in a 37° C. water bath, and RNA or DNA is extracted therefrom without delay, most preferably using a commercially-available kit (for example, Perfect RNA Total RNA Isolation Kit, obtained from Five Prime—Three Prime, Inc., Boulder, Co.), or gelatin extraction for DNA. Other methods of RNA extraction are further provided in co-owned and co-pending U.S. patent application Ser. No. 09/155,152, incorporated herein by reference in its entirety, which may similarly be adapted to DNA extraction.

Following the extraction of RNA or DNA from a bodily fluid, a fraction of which contains a drug-resistance gene mRNA, or cDNA derived therefrom, or mutated, altered, or polymorphic drug-resistance DNA, the nucleic acid or its cDNA is amplified or signal amplified in vitro. Applicable amplification assays are detailed in co-owned and co-pending U.S. patent application Ser. No. 09/155,152, as herein incorporated by reference, and include but are not limited to polymerase chain reaction amplification such as by reverse transcriptase polymerase chain reaction (RT-PCR); ligase chain reaction; DNA signal amplification methods including branched chain signal amplification; amplifiable RNA reporters; Q-beta replication; transcription-based amplification; boomerang DNA amplification; strand displacement activation; cycling probe technology; isothermal nucleic acid sequence based amplification; other self-sustained sequence replication assays; and cleavase-based amplification methods.

In preferred embodiments of the methods of the invention, drug-resistance gene mRNA is converted into cDNA using reverse transcriptase prior to in vitro amplification using methods known in the art. For example, a sample, such as 10 microL extracted serum RNA is reverse-transcribed in a 30 microL volume containing 200 Units of Moloney murine leukemia virus (MMLV) reverse transcriptase (Promega, Madison, Wis.), a reaction buffer supplied by the manufacturer, 1 mM dNTPs, 0.5 micrograms random hexamers, and 25 Units of RNAsin (Promega, Madison, Wis.). Reverse transcription is typically performed under an overlaid mineral oil layer to inhibit evaporation and incubated at room temperature for 10 minutes followed by incubation at 37° C. for one hour.

Alternatively, other methods well known in the art can be used to reverse transcribe the drug-resistance gene RNA to cDNA, as provided in these references incorporated herein by reference in their entirety, or by oligodT or primer-specific methods of reverse transcription.

Amplification primers are specific for amplifying the drug resistance protein-encoding nucleic acid. In a preferred embodiment, amplification of MRP RNA is performed by RT-PCR, preferably as set forth in Zhan et al. (Blood, 1997, 89: 3795-3800), incorporated herein by reference in its entirety, but for 45 cycles of amplification.

In this embodiment, the preferred oligonucleotide primer sequences are as follows:
5' primer sequence: CGGAAACCATCCACGAC-CCTAATCC (SEQ ID No. 1)
3' primer sequence: ACCTCCTCATTCGCATCCACCT-TGG (SEQ ID No. 2).

Alternative primers and methods of amplification of MRP RNA or cDNA, as recognized in the art, may alternatively be employed in the invention. For example, but not limitation, amplification of MRP RNA may be performed according to the methods of Mohri et al. (J. Neurooncol. 2001, 49: 105-15), incorporated herein by reference in its entirety. Amplification of MRP1 RNA, MRP2 RNA, MRP3 RNA, or MRP5 RNA may be performed according to the methods of van der Kolk et al. (Leukemia 2001, 15: 1544-53), and of Young et al. (Clin. Cancer Res. 2001, 7: 1798-804), these references incorporated herein by reference in their entirety, but with amplifications for 45 cycles preferred.

In one example of a preferred embodiment of the invention, MRP RNA is harvested from approximately 1.75 mL aliquots of serum or plasma, and RNA extracted therefrom using the Perfect RNA Total RNA Isolation Kit (Five Prime—Three Prime) performed according to manufacturer's instructions except that plasma or serum replaces tissue as noted, or by similar commercial extraction kit. From this extracted RNA preparation, 10 microL are then reverse transcribed to cDNA as described above, the resulting cDNA being diluted in water to a 20 microL volume. RT-PCR for the MRP cDNA is performed using 20 microL of the resulting MRP cDNA added to a volume of 70 microL of 1×PCR buffer as described by Zhan et al. (Blood, 1997, 89: 3795-3800) with a reaction mixture as described by Zhan et al. (Blood, 1997, 89: 3795-3800). The mixture is then amplified in a single-stage reaction in a thermocycler under a temperature profile consisting of an initial 2 minute incubation at 94° C., followed by 45 cycles of denaturation at 94° C. for 75 seconds, annealing at 55° C. for 75 seconds, and extension at 72° C. for 90 seconds for the first 35 cycles followed by 120 seconds for the last 10 cycles, followed by a final extension at 72° C. for 5 minutes. Detection of the amplified product is then achieved, for example, by gel electrophoresis through a 4% Tris-borate-EDTA (TBE) agarose gel, using ethidium bromide staining for visualization and identification of the product fragment, with the PCR product being 295 bp. Alternatively, the amplified products may thereafter be hybridized to end-labeled oligonucleotide probes and detected, such by adapting the method of Robertson et al. (Nucleic Acids Res. 27: 2291-2298, 1999) for MRP product detection.

In a preferred embodiment, amplification of MDR-1 RNA is performed by RT-PCR, preferably as set forth in Kang et al. (Blood 1995, 86:1515-24), incorporated herein by reference in its entirety. Alternative primers and methods of amplification of MDR-1 RNA or cDNA, as recognized in the art, may alternatively be employed in the invention. For example, but not limitation, amplification of MDR-1 RNA or cDNA may be performed according to the methods of Lizard-Nacol et al. (Anticancer Res. 1999, 19: 3575-81); Lyttelton et al. (Br. J. Haematol. 1994, 86: 540-6); Bosch et al. (Anticancer Res., 1997, 17: 4595-8); Kato et al. (Leuk. Lymphoma, 1994, 14: 129-35); and Pu et al. (J. Urol., 1996, 156: 271-5), these references incorporated herein by reference in their entirety.

In a preferred embodiment, amplification of thymidine phosphorylase (TP) RNA is performed by RT-PCR, preferably as set forth in Metzger et al. (Clin. Cancer Res., 1998, 4: 2371-6), incorporated herein by reference in its entirety. Alternative primers and methods of amplification of TP RNA or cDNA, as recognized in the art, may alternatively be employed in the invention.

In a preferred embodiment, amplification of dihydropyrimidine dehydrogenase (DPD) RNA is performed by RT-PCR, preferably as set forth in Uchida et al. (Int. J. Oncol., 2001, 19: 341-6), incorporated herein by reference in its entirety. Alternative primers and methods of amplification of DPD RNA or cDNA, as recognized in the art, may alternatively be employed in the invention. For example, but not limitation, amplification of DPD RNA or cDNA may be performed according to the methods of Grem et al. (Clin. Cancer Res., 2001, 7: 999-1009), Salonga et al. (Clin. Cancer Res. 2000, 6: 1322-7), and Ishikawa et al. (Clin. Cancer Res., 1999, 5: 883-9), these references incorporated by reference herein in their entirety.

In a preferred embodiment, amplification of thymidylate synthetase (TS) RNA is performed by RT-PCR, preferably as set forth in Grem et al. (Clin. Cancer Res., 2001, 7. 999-1009), incorporated herein by reference in its entirety. Alternative primers and methods of amplification of TS RNA or cDNA, as recognized in the art, may alternatively be employed in the invention. For example, but not limitation, amplification of TS RNA or cDNA may be performed according to the methods of Leichman et al. (J. Clin. Oncol., 1997, 15: 3223-9), Ehrnrooth et al. (Clin. Chim. Acta, 2000, 290: 129-44), Ehrnrooth et al. (Acta Oncol., 2000, 39: 53-7), and Kasahara et al. (Clin. Cancer Res., 2000, 6: 2707-11), these references incorporated herein by reference in their entirety.

In a preferred embodiment, amplification of glutathione S-transferase RNA or cDNA is performed by RT-PCR, preferably as set forth by Miyanishi et al. (Gastroenterology, 2001, 121: 865-74), incorporated herein by reference in its entirety. Alternative primers and methods of amplification of glutathione (GSH) S-transferase RNA or cDNA, as recognized in the art, may alternatively be employed in the invention. For example, but not limitation, amplification of GSH S-transferase RNA or cDNA may be performed according to the methods of Wang et al. (Haematologica, 2000, 85: 573-9), and Van Hille et al. (Anticancer Res., 1996, 16: 3531-6), these references incorporated by reference in their entirety.

In a preferred embodiment, amplification of mutated topoisomerase I RNA or DNA is performed by RT-PCR, preferably as set forth by Urasaki et al. (Clin. Cancer Res., 2001, 61: 1964-9), incorporated herein by reference in its entirety. Alternative primers and methods of amplification of topoisomerase I RNA, cDNA, or DNA may alternatively be employed in the invention.

In a preferred embodiment, amplification of DNA topoisomerase II alpha or beta RNA is performed by RT-PCR, preferably as set forth by Galimberti et al. (Anticancer Res., 1998, 18: 2973-6), incorporated herein by reference in its entirety. Alternative primers and methods of amplification of topoisomerase II alpha DNA, RNA, or cDNA, as recognized in the art, may alternatively be employed in the invention. For example, but not limitation, amplification of topoisomerase II alpha cDNA may be performed according to the methods of Campain et al. (Biochemistry, 1994, 33: 11327-32), and Campain et al. (Somat. Cell. Mol. Genet., 1995, 21: 451-71), there references incorporated herein by reference in their entirety.

In preferred embodiments of the invention, genetic polymorphisms of drug-resistance associated genes are detected in bodily fluids, wherein in particular said polymorphisms are detected by detecting extracellular DNA or RNA in the bodily fluid.

In a preferred embodiment, MDR-1 polymorphisms are detected by amplification and restriction fragment length polymorphism, preferably as set forth by Cascorbi et al. (Clin. Pharmacol. Ther., 2001, 69: 169-74), incorporated herein by reference in its entirety. Alternative primers and methods of amplification and/or detection of MDR-1 polymorphisms, as recognized in the art, may alternatively be employed in the invention. For example, but not limitation, the method of oligonucleotide hybridization as described by Mickley et al. (Blood, 1998, 91: 1749-56), incorporated herein by reference in its entirety, may be employed.

In a preferred embodiment, thymidylate synthase (TS) gene polymorphisms are detected by amplification, preferably as set forth by Marsh et al. (Int. J. Oncol., 2001, 19: 383-6), incorporated herein by reference in its entirety. Alternative primers and methods of amplification and detection of TS gene polymorphisms, as recognized in the art, may alternatively be employed in the invention.

In a preferred embodiment, GSH S-transferase gene polymorphisms, and GSH-associated gene polymorphisms, are detected by amplification and restriction fragment length polymorphism, preferably as set forth by Coles et al. (Pharmacogenetics, 2001, 11: 663-669), incorporated herein by reference in its entirety. Alternative primers and methods of detection of GSH-associated polymorphisms, including but not limited to GSH S-transferase polymorphisms, as recognized in the art, may alternatively be employed by the invention. For example, but not limitation, detection of GSH S-transferase polymorphisms may be performed after nucleic acid extraction according to the method of Harris et al. (Pharmacogenetics, 1998, 8: 27-31), incorporated herein by reference in its entirety. Detection of glutamate cysteine ligase catalytic subunit gene polymorphism, a GSH-associated gene polymorphism, may be performed after nucleic acid extraction according to the method of Walsh et al. (Toxicol. Sci., 2001, 61: 218-23), incorporated herein by reference in its entirety.

The invention provides for alternative methods of amplification of drug-resistance gene RNA or cDNA or DNA as would be known in the art, including signal amplification methods as known in the art. Amplification methods can further be performed in qualitative or quantitative fashion using primers specific for an internal control sequence of a reference RNA, such as glyceraldehyde-3-phosphate dehydrogenase or beta-actin, as described in the previously cited references, wherein said controls may be RNA present in the bodily fluid of both healthy individuals and individuals with cancer.

In a particularly preferred embodiment, drug-resistance gene RNA or cDNA or DNA is amplified in a quantitative amplification reaction. Quantitative amplification of drug-resistance gene RNA or cDNA or DNA is particularly advantageous because this method enables statistically-based discrimination between patients with drug-resistant neoplastic disease and populations without drug-resistant neoplasms, including normal individuals. Using these methods, quantitative distributions of drug-resistance gene RNA or DNA in bodily fluids such as blood plasma or serum are established in populations with drug-resistant and drug-sensitive neoplastic diseases, and in normal populations. Using this population information, the amount of extracellular drug-resistance gene RNA or DNA in an individual is compared with the range of amounts of extracellular drug-resistance gene RNA or DNA in said populations, resulting in a determination of whether the detected amount of extracellular drug-resistance gene RNA or DNA in an individual indicates that the individual has a probability or a predisposition for a drug-resistant neoplasm.

In alternative preferred embodiments, amplified products can be detected using other methods, including but not limited to gel electrophoresis; capillary electrophoresis; ELISA or modifications thereof, such as amplification using biotinylated or otherwise modified primers; nucleic acid hybridization using specific, detectably-labeled probes, such as fluorescent-, radioisotope-, or chromogenically-labeled probe; Southern blot analysis; Northern blot analysis; electrochemiluminescence; reverse dot blot detection; and high-performance liquid chromatography. Furthermore, detection may be performed in either a qualitative or quantitative fashion.

PCR product fragments produced using the methods of the invention can be further cloned into recombinant DNA replication vectors using standard techniques. RNA can be produced from cloned PCR products, and in some instances the RNA expressed thereby, for example but not limitation, by using the TnT Quick Coupled Transcription/Translation kit (Promega, Madison, Wis.) as directed by the manufacturer.

The methods of the invention as described above can be performed in like manner for detecting drug-resistance gene mRNA or DNA from other bodily fluids, including but not limited to whole blood, urine, effusions, ascitic fluid, saliva, cerebrospinal fluid, cervical secretions, vaginal secretions, endometrial secretions, gastrointestinal secretions, breast fluid or secretions, and bronchial secretions including sputum, and from washings or lavages. Whereas fractionation of the bodily fluid into its cellular and non-cellular components is not required for the practice of the invention, the non-cellular fraction may be separated, for example, by centrifugation or filtration of the bodily fluid.

The methods of the invention are thereby useful in the practice of a method for detecting, evaluating, or monitoring drug-resistance gene mRNA or DNA in an animal, most preferably a human at risk for developing or who has developed a premalignant, neoplastic or malignant disease consisting of cells expressing drug-resistance gene mRNA, or mutated, altered, or polymorphic drug-resistance gene DNA. The invention particularly is advantageous in evaluating therapeutic options in humans at risk for developing, or who have developed premalignancies or cancer, including but not limited to cancers of the breast, prostate, ovary, lung, cervix, colon, rectum, stomach, liver, pancreas, bladder, endometrium, kidney, brain, skin including squamous cell cancer and malignant melanoma, and esophagus, as well as premalignancies and carcinoma in-situ including but not limited to prostatic intraepithelial neoplasia (PIN), cervical dysplasia and cervical intraepithelial neoplasia (CIN), bronchial dysplasia, atypical hyperplasia of the breast, ductal carcinoma in-situ, colorectal adenoma, atypical endometrial hyperplasia, and Barrett's esophagus. The invention thereby advantageously provides methods for selecting, monitoring, and predicting the utility of specific chemotherapeutic agents.

The methods and advantageous applications of the invention can be performed using a kit as provided by the invention, wherein the kit includes primers or probes specific for drug-resistance gene cDNA synthesis or in vitro amplification or both, and/or specific probes for detecting drug-resistance gene RNA, cDNA, or DNA or in vitro amplified DNA fragments or amplified signals thereof. The kit may further include methods and reagents for extracting drug-resistance gene RNA or DNA from an extracellular bodily fluid, wherein the bodily fluid includes but is not limited to plasma or serum.

The inventive methods have significant utility in assigning and monitoring therapies, particularly anti-neoplastic therapies such as chemotherapy either as single agent therapies or in multiple agent combination therapies. The inventive methods are further useful for monitoring response, relapse, and prognosis of neoplastic diseases. Of particular value, the invention allows a determination that a therapy is therapeutically indicated both in advanced or metastatic disease states and in cases of premalignancy, early cancer, occult cancer or minimum residual disease. Thus, the invention permits selection of patients for said therapies or monitoring of therapeutic intervention, including chemoprevention, when tumor burden is high, or when tumor burden is low or when malignancy has not yet developed.

The invention further enables drug-resistance gene RNA or DNA to be evaluated in blood plasma or serum or other bodily fluid in combination with detection of other drug-resistance gene RNA or DNA, and/or in combination with other tumor-associated or tumor-derived RNA or DNA, including oncogene, tumor suppressor gene, microsatellite, or methylated DNA. Said analysis of multiple gene DNA or RNA may be performed in a concurrent or sequential fashion, such as in a multiplexed assay or in a chip-based assay, thereby increasing the sensitivity or efficacy of the assay in the detection or monitoring of chemo-resistant neoplastic diseases, or in monitoring and evaluating the development of chemoresistance, and in determining predisposition for chemoresistance and in determining a patient's prognosis.

The invention further enables the selection of patients who would benefit from therapeutic interventions designed to treat, interfere with, alleviate, mitigate, or reverse the development of drug-resistance, wherein demonstration of the drug-resistance gene nucleic acid in the bodily fluid so selects the patient.

The methods of the invention and preferred uses for the methods of the invention are more fully illustrated in the following Example. This Example illustrates certain aspects of the above-described method and advantageous results. This Example is shown by way of illustration and not by way of limitation.

EXAMPLE 1

A 54 year old man with metastatic colorectal cancer will undergo an evaluation for chemoresistance of his neoplastic disease by providing a blood plasma sample for a multiplexed assay that includes evaluation of his blood plasma for various drug-resistance gene RNAs, including MDR-1 RNA, MRP RNA, TS RNA, TP RNA, DPD RNA, and GSH S-transferase RNA. Drug-resistance gene RNA is evaluated by the methods of the invention in a quantitative manner. In addition, other tumor-associated nucleic acids, including K-ras DNA, P53 DNA, and hTERT RNA, are evaluated by the multiplexed assay. The assay indicates TS RNA, TP RNA, and DPD RNA are present in the plasma at high levels in comparison to chemosensitive tumors, particularly suggesting the patient's tumor would be resistant to 5-fluorouracil based therapies. Therapy is subsequently initiated with an alternative, non-5-fluorouracil regimen, such as with irinotecan. Serial evaluation of quantitative drug-resistance gene RNA levels in plasma, including topoisomerase I and II RNA levels, is undertaken to evaluate response to the chemotherapy regimen and to predict the development of chemoresistance.

This example demonstrates use of the invention for evaluating and monitoring drug resistance in neoplasia, for determining predisposition to drug resistance, and for selecting the preferable therapy.

What is claimed is:

1. A method for detecting extracellular RNA from all or a portion of a drug-resistance-associated gene in blood plasma or serum from a human or animal with a neoplasm in the human or animal's brain for evaluating, monitoring, predicting, treating, or making a determination of drug-resistance in the brain neoplasm, the method comprising the steps of:
   a) extracting extracellular mammalian RNA from blood plasma or serum of a human or animal with a neoplasm in the brain;
   b) amplifying or signal amplifying a portion of the extracted RNA or cDNA prepared therefrom, wherein said fraction comprises extracellular RNA from a drug-resistance-associated gene, and wherein amplification is performed qualitatively or quantitatively using primers or probes specific for said RNA or cDNA to produce an amplified product or signal; and
   c) detecting the amplified product or signal.

2. A method for detecting extracellular RNA from all or a portion of a drug-resistance-associated gene in a bodily fluid that is urine, saliva or cerebrospinal fluid from a human or animal with a neoplasm for evaluating, monitoring, predicting, treating, or making a determination of drug resistance in the neoplasm, the method comprising the steps of:
   a) extracting extracellular mammalian RNA from the bodily fluid that is urine, saliva or cerebrospinal fluid from a human or animal with a neoplasm;
   b) amplifying or signal amplifying a portion of the extracted RNA or cDNA prepared therefrom, wherein said fraction comprises extracellular RNA from a drug-resistance-associated gene, and wherein amplification is performed qualitatively or quantitatively using primers or probes specific for said RNA or cDNA to produce an amplified product or signal; and
   c) detecting the amplified product or signal.

3. The method of claim 2, wherein the bodily fluid is urine.

4. The method of claim 1, wherein the RNA is from a drug-resistance-associated gene that is multidrug resistance 1 gene, multidrug resistance-associated protein gene, multidrug resistance protein MRP1 gene, multidrug resistance protein MRP2 gene, multidrug resistance protein MRP3 gene, multidrug resistance protein MRP5 gene, topoisomerase I gene, topoisomerase II alpha gene, topoisomerase II beta gene, glutathione S-transferase gene, thymidylate synthase gene, thymidine phosphorylase gene, or dihydropyrimidine dehydrogenase gene.

5. The method of claim 2, wherein the RNA is from a drug-resistance-associated gene that is multidrug resistance 1, multidrug resistance-associated protein, multidrug resistance protein MRP1, multidrug resistance protein MRP2, multidrug resistance protein MRP3, multidrug resistance protein MRP5, topoisomerase I, topoisomerase II alpha, topoisomerase II beta, glutathione S-transferase, thymidylate synthase, thymidine phosphorylase, or dihydropyrimidine dehydrogenase.

6. The method of claim 1, wherein the amplification in step (b) is performed by an amplification method that amplifies the RNA directly, or wherein the RNA is first reverse transcribed to cDNA and wherein said cDNA is amplified, and wherein the amplification method is polymerase chain reaction, reverse transcriptase polymerase chain reaction, ligase chain reaction, signal amplification, amplifiable RNA reporters, Q-beta replication, transcription-based amplification, isothermal nucleic acid sequence based amplification, self-sustained sequence replication assays, boomerang DNA amplification, strand displacement activation, cleavase-based amplification, or cycling probe technology.

7. The method of claim 2, wherein the amplification in step (b) is performed by an amplification method that amplifies the RNA directly, or wherein the RNA is first reverse transcribed to cDNA and wherein said cDNA is amplified, and wherein the amplification method is polymerase chain reaction, reverse transcriptase polymerase chain reaction, ligase chain reaction, signal amplification, amplifiable RNA reporters, Q-beta replication, transcription-based amplification, isothermal nucleic acid sequence based amplification, self-sustained sequence replication assays, boomerang DNA amplification, strand displacement activation, cleavase-based amplification, or cycling probe technology.

8. The method of claim 1, wherein detection of amplified product in step (c) is performed using a detection method that is gel electrophoresis, capillary electrophoresis, ELISA detection using biotinylated or otherwise modified primers, labeled fluorescent or chromogenic probes, Southern blot analysis, Northern blot analysis, electrochemiluminescence, reverse dot blot detection, or high-performance liquid chromatography.

9. The method of claim 2, wherein detection of amplified product in step (c) is performed using a detection method that is gel electrophoresis, capillary electrophoresis, ELISA detection using biotinylated or otherwise modified primers, labeled fluorescent or chromogenic probes, Southern blot analysis, Northern blot analysis, electrochemiluminescence, reverse dot blot detection, or high-performance liquid chromatography.

10. The method of claim 1, wherein the neoplasm is a malignancy.

11. The method of claim 2, wherein the neoplasm is a malignancy.

12. A method of identifying a drug resistant neoplasm in a human or animal without obtaining tissue from the neoplasm, the method comprising the steps of:
 a) extracting extracellular mammalian RNA from blood plasma or serum from a human or animal with a neoplasm;
 b) amplifying or signal amplifying a portion of the extracted RNA or cDNA prepared therefrom, wherein said fraction comprises extracellular RNA from a drug-resistance-associated gene, and wherein amplification is performed qualitatively or quantitatively using primers or probes specific for said RNA or cDNA to produce an amplified product or signal; and
 c) detecting the amplified product or signal, wherein detection of the amplified product or signal in an amount greater than a reference sample from a human or animal without a drug-resistant neoplasm identifies a drug-resistant neoplasm in a human or animal.

13. The method of claim 12, wherein the RNA is from a drug-resistance-associated gene that is multidrug resistance 1, multidrug resistance-associated protein, multidrug resistance protein MRP1, multidrug resistance protein MRP2, multidrug resistance protein MRP3, multidrug resistance protein MRP5, topoisomerase I, topoisomerase II alpha, topoisomerase II beta, glutathione S-transferase, thymidylate synthase, thymidine phosphorylase, or dihydropyrimidine dehydrogenase.

14. The method of claim 12, wherein the amplification in step (b) is performed by an amplification method that amplifies the RNA directly, or wherein the RNA is first reverse transcribed to cDNA and wherein said cDNA is amplified, and wherein the amplification method is polymerase chain reaction, reverse transcriptase polymerase chain reaction, ligase chain reaction, signal amplification, amplifiable RNA reporters, Q-beta replication, transcription-based amplification, isothermal nucleic acid sequence based amplification, self-sustained sequence replication assays, boomerang DNA amplification, strand displacement activation, cleavase-based amplification, or cycling probe technology.

15. The method of claim 12, wherein detection of amplified product in step (c) is performed using a detection method that is gel electrophoresis, capillary electrophoresis, ELISA detection using biotinylated or otherwise modified primers, labeled fluorescent or chromogenic probes, Southern blot analysis, Northern blot analysis, electrochemiluminescence, reverse dot blot detection, or high-performance liquid chromatography.

16. A method of evaluating or monitoring drug resistance in a neoplasm without obtaining tissue from the neoplasm, the method comprising the steps of:
 a) extracting extracellular mammalian RNA from urine from a human or animal with a neoplasm;
 b) amplifying or signal amplifying a portion of the extracted RNA or cDNA prepared therefrom, wherein said fraction comprises extracellular RNA from a drug-resistance-associated gene, and wherein amplification is performed qualitatively or quantitatively using primers or probes specific for said RNA or cDNA to produce an amplified product or signal; and
 c) detecting the amplified product or signal.

17. The method of claim 16, wherein the RNA is from a drug-resistance-associated gene that is multidrug resistance 1, multidrug resistance-associated protein, multidrug resistance protein MRP1, multidrug resistance protein MRP2, multidrug resistance protein MRP3, multidrug resistance protein MRP5, topoisomerase I, topoisomerase II alpha, topoisomerase II beta, glutathione S-transferase, thymidylate synthase, thymidine phosphorylase, or dihydropyrimidine dehydrogenase.

18. The method of claim 16, wherein the amplification in step (b) is performed by an amplification method that amplifies the RNA directly, or wherein the RNA is first reverse transcribed to cDNA and wherein said cDNA is amplified, and wherein the amplification method is polymerase chain reaction, reverse transcriptase polymerase chain reaction, ligase chain reaction, signal amplification, amplifiable RNA reporters, Q-beta replication, transcription-based amplification, isothermal nucleic acid sequence based amplification, self-sustained sequence replication assays, boomerang DNA amplification, strand displacement activation, cleavase-based amplification, or cycling probe technology.

19. The method of claim 16, wherein detection of amplified product in step (c) is performed using a detection method that is gel electrophoresis, capillary electrophoresis, ELISA detection using biotinylated or otherwise modified primers, labeled fluorescent or chromogenic probes, Southern blot analysis, Northern blot analysis, electrochemiluminescence, reverse dot blot detection, or high-performance liquid chromatography.

20. A method for detecting extracellular RNA of all or a portion of a drug-resistance-associated gene, or cDNA reverse-transcribed from said RNA, comprising the steps of extracting extracellular RNA of all or a portion of a drug-resistance-associated gene RNA from a bodily fluid that is urine, saliva or cerebrospinal fluid, with or without converting said RNA to cDNA, hybridizing said RNA or cDNA to a detectably-labeled probe specific for said RNA or cDNA of all or a portion of a drug-resistance-associated gene, and detecting hybridization of RNA or cDNA of all or a portion of a drug-resistance-associated gene with the detectably-labeled probe.

21. A method of predicting chemoresistance in a human with a malignancy, wherein the method comprises the step of quantitatively or qualitatively comparing an amplified product produced using extracellular RNA, or cDNA therefrom, from all or a portion of a drug-resistance-associated gene from blood plasma or serum from a human with a malignancy to the amplified product produced using extracellular RNA, or cDNA therefrom, from all or a portion of a gene not associated with chemoresistance from blood plasma or serum from a human.

22. A method of predicting chemoresistance in a human with a malignancy, wherein the method comprises the step of quantitatively or qualitatively comparing an amplified product produced using extracellular RNA from all or a portion of a drug-resistance-associated gene from bodily fluid that is urine, saliva or cerebrospinal fluid from a human with a malignancy to the amplified product produced using extracellular RNA from all or a portion of a drug-resistance-associated gene from bodily fluid from a group of humans with chemoresistant malignancy, whereby chemoresistance in a human with malignancy is predicted.

23. A method according to claim 1 further comprising the step of predicting tumor resistance to a chemotherapeutic agent when an amplified signal is detected and tumor sensitivity to a chemotherapeutic agent when an amplified signal is not detected.

24. A method according to claim 2 further comprising the step of predicting tumor resistance to a chemotherapeutic agent when an amplified signal is detected and tumor sensitivity to a chemotherapeutic agent when an amplified signal is not detected.

25. A method according to claim 12 further comprising the step of predicting tumor resistance to a chemotherapeutic agent when an amplified signal is detected and tumor sensitivity to a chemotherapeutic agent when an amplified signal is not detected.

26. A method according to claim 16 further comprising the step of predicting tumor resistance to a chemotherapeutic agent when an amplified signal is detected and tumor sensitivity to a chemotherapeutic agent when an amplified signal is not detected.

27. The method of claim 23, wherein the chemotherapeutic agent is anthracyclines and anthracenediones including doxorubicin, daunorubicin, epirubicin, and mitoxantrone; antimicrotubule agents including vinca alkaloids such as vincristine and vinblastine, taxanes including paclitaxel and docetaxel; estramustine; platinum analogues such as cisplatin and carboplatin; topoisomerase II inhibitors such as VP-16and VM-26; 5-fluoropyrimidines such as 5-fluorouricil; antifolates including methotrexate; cytidine analogues; purine antimetabolites; alkylating agents including cyclophosphamide, chlorambucil, melphalan, BCNU, ifosfamide and other nitrogen mustards, busulfan, nitrosoureas; procarbazine and dacarbazine; bleomycin; dactinomycin; or camptothecins such as irinotecan and topotecan.

28. The method of claim 24, wherein the chemotherapeutic agent is anthracyclines and anthracenediones including doxorubicin, daunorubicin, epirubicin, and mitoxantrone; antimicrotubule agents including vinca alkaloids such as vincristine and vinblastine, taxanes including paclitaxel and docetaxel; estramustine; platinum analogues such as cisplatin and carboplatin; topoisomerase II inhibitors such as VP-16and VM-26; 5-fluoropyrimidines such as 5-fluorouricil; antifolates including methotrexate; cytidine analogues; purine antimetabolites; alkylating agents including cyclophosphamide, chlorambucil, melphalan, BCNU, ifosfamide and other nitrogen mustards, busulfan, nitrosoureas; procarbazine and dacarbazine; bleomycin; dactinomycin; or camptothecins such as irinotecan and topotecan.

29. The method of claim 25, wherein the chemotherapeutic agent is anthracyclines and anthracenediones including doxorubicin, daunorubicin, epirubicin, and mitoxantrone; antimicrotubule agents including vinca alkaloids such as vincristine and vinblastine, taxanes including paclitaxel and docetaxel; estramustine; platinum analogues such as cisplatin and carboplatin; topoisomerase II inhibitors such as VP-16 and VM-26; 5-fluoropyrimidines such as 5-fluorouricil; antifolates including methotrexate; cytidine analogues; purine antimetabolites; alkylating agents including cyclophosphamide, chlorambucil, melphalan, BCNU, ifosfamide and other nitrogen mustards, busulfan, nitrosoureas; procarbazine and dacarbazine; bleomycin; dactinomycin; or camptothecins such as irinotecan and topotecan.

30. The method of claim 12, wherein the chemotherapeutic agent is anthracyclines and anthracenediones including doxorubicin, daunorubicin, epirubicin, and mitoxantrone; antimicrotubule agents including vinca alkaloids such as vincristine and vinblastine, taxanes including paclitaxel and docetaxel; estramustine; platinum analogues such as cisplatin and carboplatin; topoisomerase II inhibitors such as VP-16 and VM-26; 5-fluoropyrimidines such as 5-fluorouricil; antifolates including methotrexate; cytidine analogues; purine antimetabolites; alkylating agents including cyclophosphamide, chlorambucil, melphalan, BCNU, ifosfamide and other nitrogen mustards, busulfan, nitrosoureas; procarbazine and dacarbazine; bleomycin; dactinomycin; or camptothecins such as irinotecan and topotecan.

31. The method of claim 23, further comprising the step of selecting a therapeutic agent when an amplified signal is not detected.

32. The method of claim 24, further comprising the step of selecting a therapeutic agent when an amplified signal is not detected.

33. The method of claim 25, further comprising the step of selecting a therapeutic agent when an amplified signal is not detected.

34. The method of claim 12, further comprising the step of selecting a therapeutic agent when an amplified signal is not detected.

35. The method of claim 1, further comprising the step of determining a prognosis for the human or animal.

36. The method of claim 2, further comprising the step of determining a prognosis for the human or animal.

37. The method of claim 12, further comprising the step of determining a prognosis for the human or animal.

38. The method of claim 16, further comprising the step of determining a prognosis for the human or animal.

* * * * *